United States Patent [19]

Pearce et al.

[11] Patent Number: 5,159,079
[45] Date of Patent: Oct. 27, 1992

[54] 2-PIPERIDONES AS INTERMEDIATES FOR 5-DEAZA-10-OXO- AND 5-DEAZA-10-THIO-5,6,7,8-TETRAHYDROFOLIC ACIDS

[75] Inventors: Homer L. Pearce; Mark A. Winter, both of Indianapolis, Ind.

[73] Assignee: Eli Lilly and Company, Indianapolis, Ind.

[21] Appl. No.: 810,990

[22] Filed: Dec. 20, 1991

[51] Int. Cl.$^5$ .............. C07F 7/02; C07D 211/36; C07D 401/00; A61K 31/505
[52] U.S. Cl. ......................... 546/14; 544/279
[58] Field of Search ........................... 546/243

[56] References Cited

U.S. PATENT DOCUMENTS

| | | | |
|---|---|---|---|
| 4,369,319 | 1/1983 | DeGraw et al. | 544/260 |
| 4,372,957 | 2/1983 | Duch et al. | 514/258 |
| 4,460,591 | 7/1984 | DeGraw et al. | 514/258 |
| 4,532,241 | 7/1985 | DeGraw et al. | 514/258 |
| 4,536,575 | 8/1985 | Temple et al. | 544/279 |
| 4,927,828 | 5/1990 | Taylor et al. | 514/258 |
| 5,008,391 | 4/1991 | Barnett et al. | 546/245 |
| 5,043,416 | 8/1991 | Fleet et al. | 546/243 |

FOREIGN PATENT DOCUMENTS

| | | | |
|---|---|---|---|
| 293740 | 12/1988 | European Pat. Off. | 546/243 |
| 3063383 | 6/1978 | Japan | 546/243 |
| 2844 | 7/1985 | World Int. Prop. O. | 514/258 |

OTHER PUBLICATIONS

Nair et al., *J. Med. Chem.*, 19, No. 6: 825–829 (1976).
Kim et al., *J. Med. Chem.*, 18, No. 8: 776–780 (1975).
Srinivasan et al., *J. Org. Chem.*, 45: 3746–3748 (1980).
Srinivasan et al., *J. Org. Chem.*, 46: 1777–1781 (1980).
Taylor et al., *J. Med. Chem.*, 28: 914–921 (1985).
Temple et al., *J. Org. Chem.*, 47, No. 5: 761–764 (1982).
Struck et al., *J. Med. Chem.*, 14, No. 8: 693–698 (1971).
Sirotnak et al., *Cancer Treat. Rep.*, 66: 351–358 (1982).
Temple et al., *J. Med. Chem.*, 24: 1254–1258 (1981).
Moad et al., *JACS*, 101, No. 20: 6068–6076 (1979).
DeGraw et al., *J. Heterocycl. Chem.*, 8: 105–110 (1971).
Elliot et al., *J. Med. Chem.*, 17, No. 5: 553–555 (1974).
Taylor et al., *J. Org. Chem.*, 48: 4852–4860 (1983).

*Primary Examiner*—Cecilia Tsang
*Attorney, Agent, or Firm*—Steven A. Fontana; Leroy Whitaker

[57] ABSTRACT

4-Deaza-10-oxo- and 5-deaza-10-thio-5,6,7,8-tetrahydrofolic acid derivatives are provided as agents useful for treatment susceptible neoplasms in mammals. Pharmaceutical formulations and intermediates are also provided.

11 Claims, No Drawings

2-PIPERIDONES AS INTERMEDIATES FOR 5-DEAZA-10-OXO- AND 5-DEAZA-10-THIO-5,6,7,8-TETRAHYDROFOLIC ACIDS

BACKGROUND OF THE INVENTION

The folic acid antimetabolites aminopterin and amethopterin (also known as 10-methylaminopterin or methotrexate) are antineoplastic agents. These compounds inhibit enzymatic conversions involving metabolic derivatives of folic acid. Amethopterin, for example, inhibits dihydrofolate reductase (DHFR), an enzyme necessary for the regeneration of tetrahydrofolate from dihydrofolate which is formed during the conversion of 2-deoxyuridylate to thymidylate by the enzyme thymidylate synthetase.

Other derivatives of folic acid and aminopterin have been synthesized and tested as antimetabolites. Among these are compounds in which a methylene or methylidene group occupies a position in the molecule normally occupied by an imino or nitrilo group, respectively. These derivatives have varying degrees of antimetabolic activity. 10-Deazaaminopterin is highly active (Sirotnak et al., Cancer Treat. Rep. 62: 1047 (1978)) and 5-deazaaminopterin has activity similar to that of amethopterin (Taylor et al., J. Org. Chem., 48: 4842 (1983)). 8,10-Dideazaaminopterin is reported to be antimetabolically active (U.S. Pat. No. 4,460,591) and 5,8,10-trideazaaminopterin exhibits activity against mouse L1210 leukemia (Yan et al., J. Heterocycl. Chem., 16: 541 (1979)). 10-Deazafolic acid, on the other hand, shows no significant activity (Struck et al., J. Med. Chem., 14: 693 (1971)) and 5-deazafolic acid is only weakly cytotoxic. 8,10-Dideazafolic acid is only marginally effective as a dihydrofolate reductase inhibitor (De Graw et al., "Chemistry and Biology of Pteridines", Elsevier, 229 (1979)) and 5,8,10-trideazafolic acid also shows only marginal activity against mouse L1210 leukemia (Oatis et al., J. Med. Chem., 20: 1393 (1977)). 5,10-Dideazaaminopterin and 5,10-dideaza-5,6,7,8-tetrahydroaminopterin, and the corresponding 5,10-dideazafolic acid derivatives are reported by Taylor et al., J. Med. Chem., 28, No. 7: 914 (1985).

Additional derivatives of folic acid and aminopterin include: 10-oxafolic acid and 7,8-dihydro-10-oxafolic acid which are not effective inhibitors of DCM resistant Lactobacillus casei dihydrofolate reductase; 10-oxaaminopterin and 7,8-dihydro-10-thiofolic acid, which are potent DHFR inhibitors (Nair et al., J. Med. Chem., 19, No. 6: 825 (1976)); 10-thiafolic acid, a moderate DHFR inhibitor; and a very potent dihydrofolate reductase inhibitor, 10-thiaaminopterin (Kim et al., J. Med. Chem., 18, No. 8: 776 (1975)).

This invention provides novel folic acid derivatives, their composition and use. In particular, this invention concerns 5-deaza-10-oxo- and 5-deaza-10-thio-5,6,7,8-tetrahydrofolic acid, intermediates for their preparation, pharmaceutical formulations containing the named compounds, and their use for the treatment of susceptible neoplasms.

SUMMARY OF THE INVENTION

This invention relates to folic acid derivatives of the formula

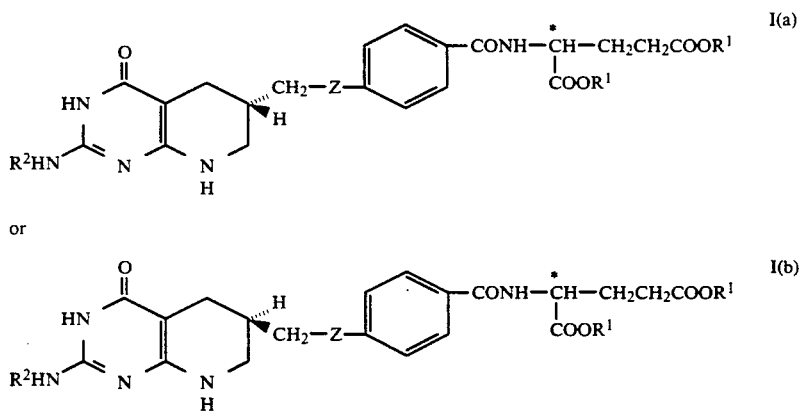

wherein
Z is O or S;
$R^1$ is H or a carboxyl protecting group;
$R^2$ is H or an amino protecting group; and
the configuration about the carbon atom designated * is L;
or a pharmaceutically acceptable salt thereof.

This invention also relates to compounds of the following formulae:

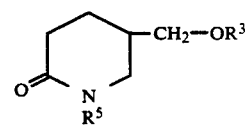

wherein
$R^3$ is H or a hydroxyl protecting group; and
$R^5$ is H or an amino protecting group; and

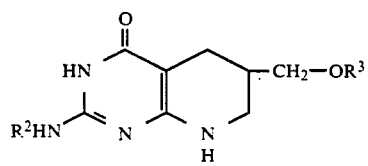

wherein
$R^2$ and $R^3$ are as defined above; and

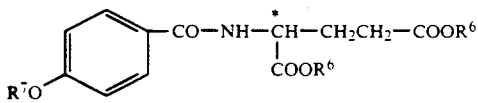

wherein
$R^6$ is a carboxyl protecting group;
$R^7$ is a hydroxyl protecting group; and
the configuration about the carbon atom designated * is L.

Also included in this invention are methods and compositions for the use of compounds of formula I for the treatment of susceptible neoplasms.

DETAILED DESCRIPTION OF THE INVENTION

The present invention pertains to the individual diastereomers and to the diastereomeric mixture of folic acid derivatives of formula I(a) and I(b).

The compounds of formula I(a) and I(b) in which each of $R^1$ and $R^2$ is hydrogen, and the salts thereof, have an inhibitory effect on one or more enzymes which utilize folic acid and, in particular, metabolic derivatives of folic acid, as a substrate. Neoplasms in mammals which depend upon such enzymes for growth are susceptible to treatment when an effective amount of the above compounds is administered. The term "effective amount" means that dosage of active substance to provide inhibition of such enzymes. Thus, the compounds of formula I(a) and I(b) are useful for treating susceptible neoplasms in mammals.

The compounds of formula I(a) and I(b), in which $R^1$ is a carboxyl protecting group or $R^2$ is an amino protecting group, are chemical intermediates useful in the preparation of the final compounds. Similarly, compounds in which $R^1$ is a carboxyl protecting group and $R^2$ is an amino protecting group are also useful as such chemical intermediates.

The compounds of formula I(a) and I(b) exist in tautomeric equilibrium with the corresponding 4-hydroxy compound:

tyl, n-hexyl, isohexyl, 3-methylpentyl, 2,3-dimethylbutyl, and the like.

The term "lower alkanoyl of from 1 to 8 carbon atoms" refers to straight or branched univalent aliphatic acyl groups of 1-8 carbon atoms including, for example, formyl, acetyl, propionyl, butyryl, α-methylpropionyl, valeryl, α-methylbutyryl, β-methylbutyryl, pivaloyl, octanoyl, and the like.

The term "tri-lower alkylsilyl" contemplates tri-isopropylsilyl, tri-methylsilyl, triethylsilyl, and t-butyldimethylsilyl.

The protecting groups of $R^1$, $R^2$ and $R^3$, as utilized herein, denote groups which generally are not found in the final therapeutic compounds but which are intentionally introduced during a portion of the synthetic process to protect a group which otherwise might react in the course of chemical manipulations, and are then removed at a later stage of the synthesis. Since compounds bearing such protecting groups are of importance primarily as chemical intermediates (although some derivatives also exhibit biological activity), their precise structure is not critical. Numerous reactions for the formation and removal of such protecting groups are described in a number of standard works including, for example, "Protective Groups in Organic Chemistry", Plenum Press, (London and New York, 1973); Greene, Th. W., "Protective Groups in Organic Synthesis", Wiley, (New York, 1981); and "The Peptides", Vol. I, Schrööder and Lubke, Academic Press, (London and New York, 1965).

A carboxyl group can be protected as an ester group which is selectively removable under sufficiently mild conditions so as to not disrupt the desired structure of the molecule, especially a lower alkyl ester such as ethyl or, particularly, methyl. Other lower alkyl esters include those which are branched at the 1-position such as t-butyl, and those which are substituted in the 1 or 2-position with (i) lower alkoxy, such as methoxymethyl, 1-methoxyethyl, ethoxymethyl, and the like; (ii) lower alkylthio, such as methylthiomethyl, 1-ethylthioethyl and the like; (iii) halogen, such as 2,2,2-trichloroethyl, 2-bromoethyl, 2-iodoethoxycarbonyl, and the like; (iv)

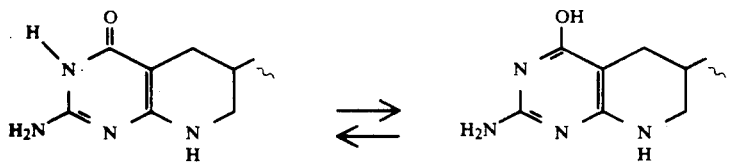

For convenience, the 4(3H)-oxo form is depicted for formula I(a) and I(b) and the corresponding nomenclature is used throughout this specification. However, it is understood that such depictions include the corresponding tautomeric 3,4-dehydro-4-hydroxy form.

The following definitions refer to the various terms used above and throughout the disclosure.

The term "halo" refers to fluoro, chloro, bromo, and iodo.

The term "lower alkyl of from 1 to 4 carbon atoms" refers to the straight or branched aliphatic chains of 1-4 carbon atoms including methyl, ethyl, propyl, isopropyl, n-butyl, isobutyl, sec.-butyl and tert.-butyl.

The term "lower alkyl of from 1 to 6 carbon atoms" refers to those aliphatic chains of from 1 to 4 carbon atoms plus the straight and branched aliphatic chains of 5-6 carbon atoms including n-pentyl, isopentyl, neopen- 1, 2 3 phenyl groups, each of which can be unsubstituted or mono-, di- or tri-substituted with, for example, lower alkyl such as t-butyl, lower alkoxy such as methoxy, hydroxy, halo such as chloro, and nitro such as 4-nitrobenzyl; or (v) aroyl, such as phenacyl. A carboxyl group can also be protected in the form of an organic silyl group such as tri-lower alkylsilyl, as for example, trimethylsilyloxy.

Amino groups similarly can be protected. Typically, an amide utilizing an acyl group which is selectively removable under mild conditions such as formyl, a lower alkanoyl group which is branched at the 1-position including, especially, a tertiary alkanoyl such as pivaloyl, or a lower alkanoyl group which is substituted in the 1-position such as trifluoroacetyl are useful. Other amino protecting groups include N-alkoxycarbonyls such as N-methoxycarbonyl, N-ethoxycarbonyl, N-(t- butyloxycarbonyl), N-diisopropyl-methoxycarbonyl and, especially, N-(t-butyloxycarbonyl).

Hydroxyl groups can be protected by an organic silyl group (See also, Colvin, E. W., "Silicon Reagents in Organic Synthesis", Academic Press, (London and New York 1988). Particularly useful are alkyl(diphenylsilyl) ethers such as t-butyldiphenylsilyl ether and tri-lower alkylsilyls which are selectively removable under sufficiently mild conditions not to disrupt the desired structure of the molecule but which will also withstand the selective removal of an amino protecting group. Preferred tri-lower alkylsilyl hydroxyl protecting groups include tri-isopropylsilyl, trimethylsilyl, triethylsilyl, and, especially, t-butyldimethylsilyl.

The compounds of formula I(a) and I(b) in which each of $R^1$ and $R^2$ is hydrogen often can be employed in the form of a pharmaceutically acceptable salt. Such forms, including hydrates thereof, are frequently crystalline and therefore useful for forming solutions or formulating pharmaceutical compositions. Pharmaceutically acceptable salts with bases include those formed from the alkali metals, alkaline earth metals, non-toxic metals, ammonium, and mono-, di- and tri-substituted amines. Examples of such salts include sodium, potassium, lithium, calcium, magnesium, aluminum, zinc, ammonium, trimethylammonium, triethanolammonium, pyridinium, substituted pyridinium and like salts. The mono- and, particularly, the di-sodium salts of the above-mentioned compounds are especially useful.

In one process, intermediates represented by the foregoing formula II are prepared as shown below in Scheme I.

Scheme I

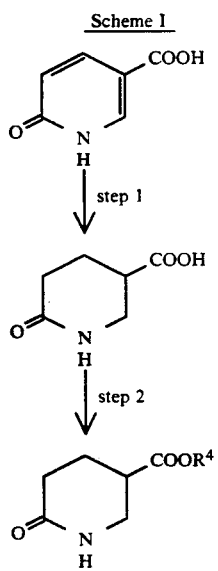

wherein $R^4$ is a carboxyl protecting group.

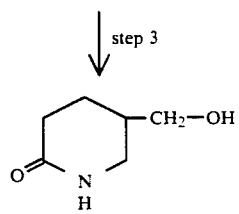

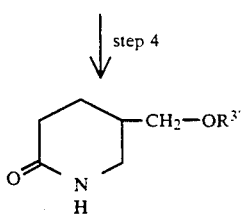

wherein $R^{3'}$ is a hydroxyl protecting group.

Generally, the carboxylic acid on 6-oxonicotinic acid, formula (a), is first converted to its sodium salt by adding a weak base, preferably sodium bicarbonate, to a suspension of compound (a) in water, and then catalytically hydrogenated (step 1). Suitable hydrogenation catalysts include noble metals and noble metal oxides such as palladium, platinum, or rhodium oxide on a support such as carbon or calcium oxide. However, ruthenium on an alumina support is preferred. The resulting compound (b) is then esterified with the desired ester forming group which serves as a carboxyl protecting group (step 2). For example, the free acid of (b) is esterified with an alkanol in the presence of thionyl chloride to form alkyl esters represented by compounds of formula (c). $C_1$–$C_6$ alkyl esters are preferred carboxyl protecting groups, and the ethyl ester is especially preferred. To form compound (d), compounds of formula (c) are reduced using standard techniques, but adding lithium aluminum hydride to a solution of (c) in tetrahydrofuran (THF) is preferred (step 3).

In step 4, the hydroxyl group of compound (d) is protected, forming compounds of formula (e). Conventional hydroxyl protecting groups and techniques for such protection may be utilized. However, the protecting group need be selectively removable under sufficiently mild conditions so as not to disrupt the desired structure, but also needs to withstand the selective removal of amino protecting groups and subsequent cyclization as shown in Scheme II below.

Compounds of formulae (d) and (e) are novel intermediates which are useful in the synthesis of compounds of formula I(a) and I(b). These compounds are encompassed within Formula II above.

In Scheme II, the amide of compounds of formula (e) is protected by an amino protecting group to give compounds of formula (f) (step 5). These novel compounds are also encompassed within Formula II above. N-alkoxycarbonyl protecting groups are preferred, while N-t-butyloxycarbonyl is especially preferred.

Acylation is then accomplished using conventional techniques to form compounds of formula (g) (step 6). Preferably, a strong kinetic base such as lithium 2,2,6,6-tetramethylpiperidide, lithium hexamethyl disilazide or, especially, lithium diisopropylamide (LDA) is used to form the imidate anion of (f), which is then reacted with a compound of the formula

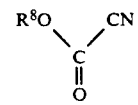

wherein $R^8$ is a lower alkyl of from 1 to 4 carbon atoms, giving compounds of formula (g). Compounds of formula (w) are known as Mander's reagents.

In step 7, the amino protecting group ($R^5$) of (g) is selectively cleaved and the resulting compounds of formula (h) are methylated giving compounds of formula (i) (step 8). Selective cleavage is accomplished by adding a strong, anhydrous acid, such as anhydrous trifluoroacetic acid, to (h) in an anhydrous solvent such as dichloromethane. By conducting this cleavage under anhydrous conditions, the hydroxyl protecting group ($R^3$) remains intact. Methylation is accomplished by adding a methylating agent such as methyl iodide, trimethylsulfoxonium iodide or, particularly, trimethyloxonium fluoroborate to a mixture of (h) in an anhydrous solvent such as dichloromethane.

Cyclization of (i) to form the pyrido[2,3-d]pyrimidine represented by compounds of formula (j) (step 9), a versatile and critical intermediate, is accomplished by reacting a compound of formula (i) with guanidine free base, in the absence of solvent or other reagents, heated under nitrogen, cooled, precipitated and filtered (See, e.g. Example 9).

Regarding compounds of formula (k), $R^{2\prime}$ represents a conventional amino protecting group. Preferred protecting groups are $C_1$-$C_8$ alkanoyls, and pivaloyl is especially preferred (step 10).

In step 11, the hydroxyl protecting group of (k) is removed by adding a weak acid such as glacial acetic acid to (k) in an inert solvent such as tetrahydrofuran (THF). The resulting compounds of formula (l), in addition to compounds of formulae (k) and (j), each are novel intermediates which are further useful in the synthesis of antineoplastic compounds of formula I(a) and I(b). Compounds of formulae (j), (k) and (l) are encompassed within formula III above.

Scheme II compound (e)

↓ Step 5

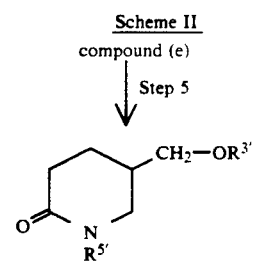 (f)

wherein
$R^{3\prime}$ is as defined above; and
$R^{5\prime}$ is an amino protecting group.

↓ Step 6

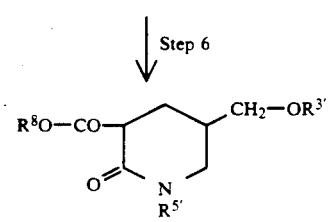 (g)

wherein $R^{3\prime}$, $R^{5\prime}$ and $R^8$ are as defined above.

↓ Step 7

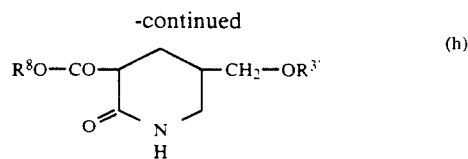 (h)

wherein $R^{3\prime}$ and $R^8$ are as defined above.

↓ Step 8

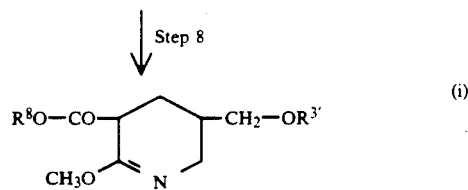 (i)

wherein $R^{3\prime}$ and $R^8$ are as defined above.

↓ Step 9

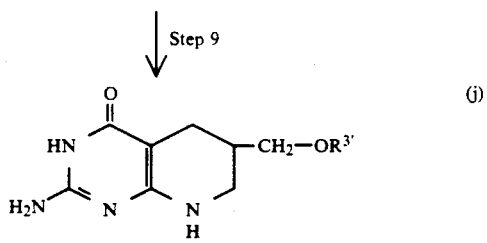 (j)

wherein $R^{3\prime}$ is as defined above.

↓ Step 10

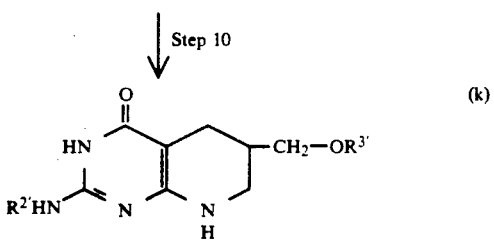 (k)

wherein
$R^{3\prime}$ is as defined above; and
$R^{2\prime}$ is an amino protecting group.

↓ Step 11

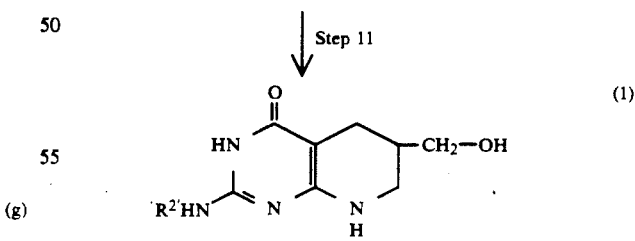 (l)

wherein $R^{2\prime}$ is as defined above.

In Scheme III, preferred hydroxyl protecting groups ($R^7$) on compounds of formulae (m) and (n) are benzyl or substituted benzyl wherein the substituted benzyl bears 1, 2 or 3 substituents selected from a group consisting of halo, trifluoromethyl and lower alkyl of from 1 to 6 carbon atoms. Compounds of formula (m) are coupled with a protected glutamic acid derivative of the formula $$H_2N-\overset{*}{C}H-CH_2CH_2COOR^6 \quad\quad (v)$$
$$\quad\quad\quad |$$
$$\quad\quad COOR^6$$

wherein $R^6$ is as defined above, using conventional condensation techniques for forming peptide bonds (step 12), giving compounds of formula (n). In this step, the acid chloride of the benzoic acid component of (m) is first formed by adding an appropriate chlorinating agent such as oxalyl chloride or, particularly, thionyl chloride, plus one drop of N,N-dimethylformamide (DMF), to (m) in an inert solvent. The condensation is completed by adding the L-glutamic acid derivative of the above formula to the mixture of the benzoic acid chloride in an anhydrous inert solvent, immediately followed by drop-wise addition of an appropriate base. Preferred bases include pyridine, potassium carbonate, and, especially, triethylamine. Preferred carboxyl protecting groups are $C_1-C_6$ alkyl, especially methyl.

In the above glutamic acid derivative, the absolute configuration about the carbon atom designated * is L, being the same absolute configuration as that about the corresponding alpha carbon in alanine.

The hydroxyl protecting group of (n) is then removed using standard techniques (step 13), giving compounds of formula (o). The preferred procedure is taught in Example 15.

Compounds of formula (n) are novel intermediates for the preparation of compounds of formula I(a) and I(b), and are encompassed within formula IV above.

_Scheme III_

(m) $R^7O-C_6H_4-COOH$ wherein $R^7$ is as defined above.

↓ step 12

(n) $R^7O-C_6H_4-CONH-\overset{*}{C}H(COOR^6)-CH_2CH_2COOR^6$ wherein $R^6$, $R^7$ and the designation "*" are as defined above.

↓ step 13

(o) $HO-C_6H_4-CONH-\overset{*}{C}H(COOR^6)-CH_2CH_2COOR^6$ wherein $R^6$ and the designation "*" are as defined above.

In Scheme IV, a compound of formula (l) and a compound of formula (o) are coupled to form compounds of formula (p) (step 14). Preferably, compounds of formula (p) are derived by first adding (l) to a solution of (o) and triphenylphosphine in anhydrous THF, followed by the addition of diethyl azodicarboxylate (DEAD). With this procedure, the hydroxyl group of the 6-hydroxymethyl substituent of (l) reacts with triphenylphosphine to form a phosphonium oxide leaving group which is subsequently displaced by the hydroxybenzoyl group of the glutamic acid derivative (v). Step 14 may be accomplished in the absence of DEAD, but the presence of DEAD substantially increases the yield of compounds of formula (p).

The compounds of formula (p) are then subjected to hydrolysis to remove the protecting groups $R^{2'}$ and $R^6$ (step 15). This is conducted at normal temperatures utilizing aqueous acids or bases. Preferred bases are alkali metal hydroxides such as sodium hydroxide, optionally in the presence of water miscible organic solvents such as methanol, ethanol, tetrahydrofuran, dimethylformamide, and the like, while hydrochloric acid is the preferred acid. When base is used, the cationic moiety of the salt is liberated and the product is formed as the dicationic glutamate salt which can be readily precipitated by adjustment of pH, as through acidification with, for example, hydrochloric acid. The resulting products generally are high melting crystalline or microcrystalline solids.

_Scheme IV_ compound (l) + compound (o)

↓ step 14

(p) pyrido-pyrimidine-$CH_2-O-C_6H_4-CONH-\overset{*}{C}H(COOR^6)-CH_2CH_2COOR^6$ wherein $R^{2'}$ and $R^6$ and the designation "*" are as defined above.

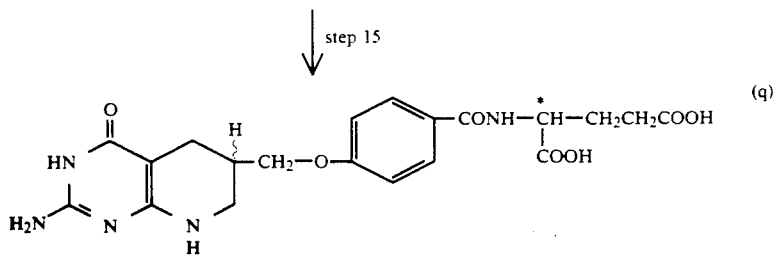

(q)

wherein the designation "*" is as defined above.

Compounds of formula I(a) and I(b), wherein Z is S, are synthesized following the procedures outlined in Scheme V below. In this Scheme, the synthesis of a compound of formula (r) is known in the art (See, e.g., Campaigne, et al. *J. Org. Chem.*, 27; 2835 (1962).

Coupling compound (r) to the glutamic acid derivative defined above, (v) (step 16), is similar to step 12 of Scheme III. Generally, the acid chloride of (r) is formed by addition of an appropriate chlorinating agent such as thionyl chloride, to a suspension of (r) in an inert solvent such as dichloroethane. The acid chloride is then dissolved in an appropriate inert solvent such as dichloromethane and an equivalent amount of an appropriate base such as triethylamine is drop-wise added. Addition of the acid scavenger allows for substitution of the acid chloride by the L-glutamic acid derivative (v), resulting in the formation of compounds of formula (s).

Compounds of formula (s) are then further coupled with a compound of formula (l) (step 17) followed by the hydrolysis of protecting groups $R^{2'}$ and $R^6$ (step 18) by the method described above for step 15.

Step 17 is accomplished by adding a compound of formula (s) to a solution of a compound of formula (l) and tri-n-butylphosphine in DMF. Particularly, tri-n-butylphosphine cleaves the disulfide bond of (s) and forms a phosphonium salt which in turn reacts with the hydroxymethyl substituent of (l). The resulting phosphoric ester forms a strong leaving group which is nucleophilically displaced by the carboxyphenylsulfinyl glutamic acid derivative.

Scheme V

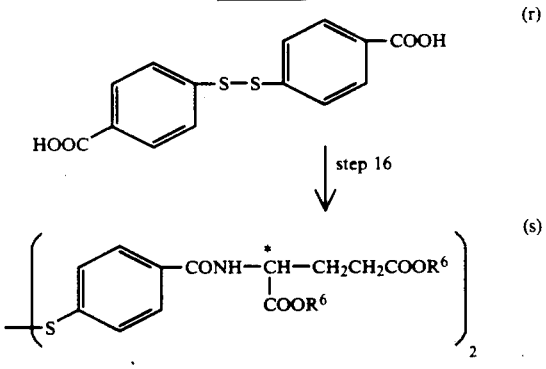

wherein $R^6$ and the designation "*" is as defined above.

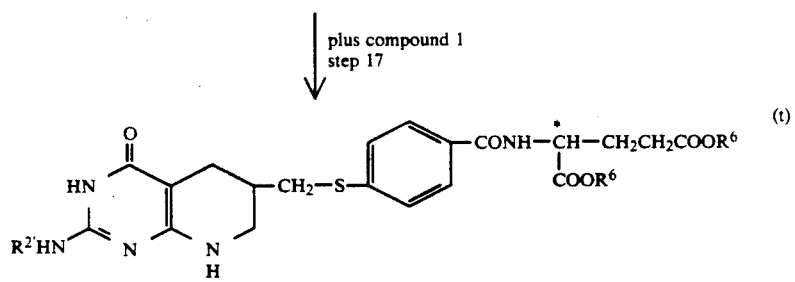

wherein $R^{2'}$, $R^6$ and the designation "*" are as defined above.

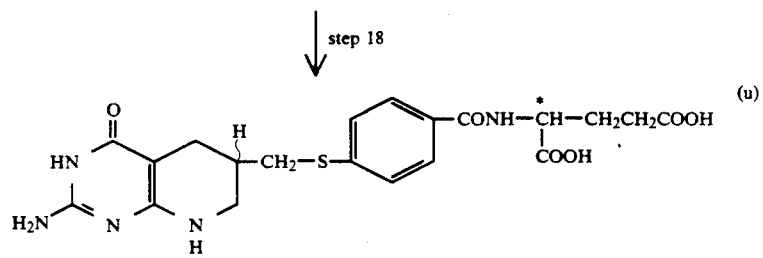

wherein the designation "*" is as defined above.

As mentioned above, the absolute configuration about the carbon atom designated * in the glutamic acid derivative (v) is L. The carbon atom in the 6-position of the 5,6,7,8-tetrahydropyrido[2,3-d]pyrimidine ring system also is a chiral center, leading to d,L- and l,L-diastereoisomers. Both forms, which can be separated mechanically as by chromatography, are within the scope of the invention. Alternatively, the individual diastereoisomers can be separated by forming diastereomeric salts with a chiral acid such as the individual enantiomers of 10-camphorsulfonic acid, camphoric acid, alphabromocamphoric acid, methoxyacetic acid, tartaric acid, diacetyltartaric acid, malic acid, pyrrolidone-5-carboxylic acid, and the like, and then freeing the individual diastereomeric bases, optionally repeating the process, so as to obtain each substantially free from the others; e.g., in a form having an optical purity of greater than 95%. This separation can be effected before or after removal of any protecting groups.

As noted, the compounds of this invention have an effect on one or more enzymes which utilize folic acid, and in particular, metabolic derivatives of folic acid as a substrate. For example, 5-deaza-10-oxo- and 5-deaza-10-thio-5,6,7,8-tetrahydrofolic acid demonstrate potent inhibitory effects against growth of human T-cells derived from lymphoblastic leukemia cells (CCRF-CEM), exhibiting $IC_{50}$s of 0.006 $\mu$g/mL and 0.003 $\mu$g/mL, respectively. Cytotoxicity is reversed by addition of purines such as hypoxanthine or by addition of aminoimidazolecarboxamide (AICA) indicating that this compound is a GAR-transformylase inhibitor. These compounds can be used, under the supervision of qualified professionals, to inhibit the growth of neoplasms including choriocarcinoma, leukemia, adenocarcinoma of the female breast, epidermid cancers of the head and neck, squamous or small-cell lung cancer, and various lymphosarcomas. The compounds can also be used to treat mycosis fungoides and psoriasis.

The compounds can be administered orally but preferably are administered parenterally, alone or in combination with other therapeutic agents including other antineoplastic agents, steroids, etc., to a mammal suffering from neoplasm and in need of treatment. Parenteral routes of administration include intramuscular, intrathecal, intravenous and intra-arterial. Dosage regimens must be titrated to the particular neoplasm, the condition of the patient, and the response. However, doses generally will be from about 10 to about 100 mg/day for 5-10 days or single daily administration of 250-500 mg., repeated periodically such as every 14 days. Oral dosage forms, including tablets and capsules, contain from 1 to 100 mg. of drug per unit dosage. Isotonic saline solutions containing 1-100 mg/mL can be used for parenteral administration.

The following preparations and specific examples are shown to further assist the reader in preparing the compounds of the present invention. However, these specific examples are not intended to be limiting on the scope of the invention.

EXAMPLE 1

5-Carboxy-2-piperidone

To a suspension of 10.0 g of 6-hydroxynicotinic acid in 200 ml water were added 6.5 g of sodium bicarbonate. The resulting solution was subjected to 500 psig hydrogen at 100° C. for 12 hours in the presence of 2.5 g ruthenium on alumina. The catalyst was removed by filtration. The filtrate was acidified to pH 4 with 6N HCl and evaporated to a colorless solid (~15 g). The solid was treated with 40 ml methanol and filtered to remove most of the sodium chloride. The filtrate was evaporated to give 7.5 g of the title compound: MS m/z 143 (M+); 300-MHz $^1$H NMR (DMSO-d$_6$) $\delta$1.62-1.77 (m, 1 H), 1.83-1.97 (m, 1 H), 2.00-2.21 (m, 2 H), 2.23-2.35 (m, 1 H), 3.21 (d, J=8 Hz, 2 H), 7, 28 (s, 1 H).

EXAMPLE 2

5-Ethoxycarbonyl-2-piperidone

To a suspension of 250 g of 5-carboxy-2-piperidone in 2.5 liters of punctilious ethanol were added 500 g of thionyl chloride at 22° C. Stir for 18 hours. The resulting solution was evaporated to dryness and the residue triturated with ether to give 233 g of the title compound: MS m/z 171 (M+), 142, 126, 115, 98; 300-MHz $^1$H NMR (DMSO-d$_6$) $\delta$1.21 (t, J=7 Hz, 3 H), 1.78-1.92 (m, 1 H), 1.95-2.08 (m, 1 H), 2.15-2.31 (m, 2 H), 2.78-2.89 (m, 1 H), 3.25-3.40 (m, 2 H), 4.12 (t, J=7 Hz, 2 H), 7.95 (s, 1 H).

EXAMPLE 3

5-Hydroxymethyl-2-piperidone

Solid lithium aluminum hydride (3.5 g) was added slowly to a solution of 15.0 g 5-ethoxycarbonyl-2-piperidone in 350 ml THF at −4° C. After stirring for 1 hour under a nitrogen atmosphere, the reaction was decomposed by dropwise addition of 3.5 ml water, 3.5 ml 5N NaOH and 10.5 ml water. The mixture was filtered and the granular precipitate washed with 100 ml THF. Evaporation of the combined filtrate and washings provided 6.0 g of the title compound: MS m/z 130 (M++1), 129 (M+), 128 (M+−1) 101, 73, 56; 90-MHz $^1$H NMR (CDCl$_3$) $\delta$1.42-1.60 (m, 1 H), 1.60-2.05 (m, 2 H), 2.10-2.47 (m, 2 H), 3.05 (t, J=9 Hz, 1 H), 3.21-3.58 (m, 4 H), 6.85 (s, 1 H).

EXAMPLE 4

5 [t-Butyl(dimethyl)silyloxymethyl]-2-piperidone

To a solution of 5.8 g tert-butyl(dimethyl)silyl chloride and 5.0 g of 5-hydroxymethyl-2-piperidone in 150 ml of anhydrous DMF was added 5.3 g of imidazole. After stirring for 36 hours at 22° C., the mixture was evaporated under vacuum to remove most of the DMF. Following the addition of water, the residue was extracted with three portions of ethyl acetate. The combined organic extracts were washed with water, 0.5N HCl, water and brine, dried over magnesium sulfate and evaporated. The resulting oil was chromatographed over silica gel eluting with 5% methanol in chloroform to give 4.7 g of the title compound as an oil: MS m/z 244 (M+), 186 [M+-58(t-butyl)]; 300-MHz $^1$H NMR (CDCl$_3$) $\delta$0.05 (s, 6 H), 0.85 (s, 9 H), 1.42-1.57 (m, 1 H), 1.77-1.88 (m, 1 H), 1.89-2.03 (m, 1 H), 2.25- 2.45 (m, 2 H), 3.03 (t, J=9 Hz, 1 H), 3.30-3.41 (m, 1 H), 3.45-3.59 (m, 2 H), 5.95 (s, 1 H).

EXAMPLE 5

N-(t-Butyloxycarbonyl)-5-[t-butyl(dimethyl)silyloxymethyl]-2-piperidone

To a solution of 3.1 g di-t-butyl dicarbonate and 3.2 g 5 [t-butyl(dimethyl)-silyloxymethyl]-2-piperidone in anhydrous THF was added 0.16 g 4-N,N-dimethylaminopyridine (DMAP). After stirring for 18 hours at 22° C., the mixture was evaporated under vacuum to remove most of the THF. Following the addition of water, the residue was extracted with three portions of ethyl acetate. The combined organic extracts were washed with a saturated sodium bicarbonate solution and brine, dried over magnesium sulfate and evaporated. The resulting oil was chromatographed over silica gel eluting with 10% ethyl acetate in toluene to give 3.5 g of the title compound as an oil: MS m/z 270 [M+−74(t-butyloxy)]; 90 MHz ¹H NMR (CDCl₃) δ0.08 (s, 6 H), 0.87 (s, 9 H), 1.38–1.51 (m, 1 H), 1.48 (s, 9 H), 1.62–2.09 (m, 2 H), 2.29–2.56 (m, 2 H), 3.10–3.48 (m, 3 H), 3.71–3.92 (m, 1 H).

EXAMPLE 6

3-Ethoxycarbonyl-N-(t-butyloxycarbonyl)-5-[t-butyl(dimethyl)silyloxymethyl]-2-piperidone To a solution of 0.65 g diisopropylamine in 40 ml anhydrous THF at −78° C. were added 6.4 ml of 1.0M n-butyllithium in hexane. After stirring for 15 minutes under nitrogen, the temperature was increased to −20° C. and a solution of 2.0 g of N-(t-BOC)-5-[t-butyl(dimethyl)silyloxymethyl]-2-piperidone in 5 ml THF was added. After stirring for 90 minutes, the temperature was reduced to −78° C. and a solution of 0.64 g of ethyl cyanoformate in 5 ml THF was added. The reaction solution was stirred for an additional 15 minutes and then poured into water and extracted with three portions of ethyl acetate. The combined organic extracts were washed with brine, dried over magnesium sulfate and evaporated. The resulting oil was chromatographed over silica gel eluting with 10% ethyl acetate in toluene to give 1.8 g of the title compound: MS m/z 358 [M+−58(t-butyl)], 342 [M+−74 (t-butyloxy)]; 300-MHz ¹H NMR (CDCl₃) δ0.05 (s, 6 H), 0.89 s, 9 H), 1.27 (t, J=8 Hz, 3 H), 1.52 (s, 9 H), 1.72–1.90 (m, 1 H), 2.05–2.18 (m, 1 H), 2.20–2.31 (m, 1 H), 3.39–3.62 (m, 4 H), 3.80 (d of d, J=12, 4 Hz, ½ H), 3.94 (d of d, J=12, 5 Hz, ½ H), 4.17–4.30 (q, J=8 Hz, 2 H).

EXAMPLE 7

3-Carboethoxy-5-[t-butyl(dimethyl)silyloxymethyl]-2-piperidone

To a solution of 1.2 g 3-carboethoxy-N-(t-BOC)-5-[t-butyl(dimethyl)silyloxymethyl]-2-piperidone in 6 ml anhydrous dichloromethane at 22° C. were added 0.66 g of anhydrous trifluoroacetic acid. The solution was stirred for 1 hour and then poured into a saturated sodium bicarbonate solution and extracted with three portions of dichloromethane. The combined organic extracts were washed with brine, dried over magnesium sulfate and evaporated to give 0.90 g of the title compound: MS m/z 316 (M+), 258 [M+−58(t-butyl)], 230; 300-MHz ¹H NMR (CDCl₃) δ0.05 (s, 6 H), 0.91 (s, 9 H), 1.31 (t, J=7 Hz, 3 H), 1.80–1.91 (m, H), 2.08–2.19 (m, 1 H), 2.21–2.35 (m, 1 H), 3.15 (t, J=12 Hz, 1 H), 3.38–3.59 (m, 3 H), 3.61–3.68 (m, 1 H), 4.21–4.30 (m, 2 H), 5.97 (b s, 1 H).

EXAMPLE 8

2-Methoxy-3-carboethoxy-5-[t-butyl(dimethyl)silyloxymethyl]-3,4,5,6-tetrahydropyridine To a solution of 14.9 g 3-carboethoxy-5-[t-butyl(dimethyl)silyloxymethyl]-2-piperidone in 400 ml anhydrous dichloromethane at 4° C. were added 7.7 g of trimethyloxonium tetrafluoroborate. The mixture was first stirred for 90 minutes at 4° C. and then for 1 hour at 22° C. The resulting solution was poured into a saturated solution of sodium bicarbonate and extracted with three portions of dichloromethane. The combined organic extracts were washed with water and brine, dried over magnesium sulfate and evaporated to give 13.8 g of the title compound: 300-MHz ¹H NMR (CDCl₃) δ0.04 (s, 6 H), 0.88 (s, 0 9 H), 1.25 (t, J=7 Hz, 3 H), 1.51–2.18 (m, 3 H), 3.11–3.32 (m, 2 H), 3.48–3.56 (m, 2 H), 3.60–3.76 (m, 4 H), 4.19 (t, J=7 Hz, 2 H).

EXAMPLE 9

2-Amino-4-hydroxy-6-[t-butyl(dimethyl)silyloxymethyl]-5,6,7,8-tetrahydropyrido[2,3-d]pyrimidine A mixture of 9.8 g of guanidine free base and 13.8 g of 2-methoxy-3-carboethoxy-5-[t-butyl(dimethyl)silyloxymethyl]-3,4,5,6-tetrahydropyridine was heated at 90° C. under nitrogen for 18 hours. The mixture was cooled to room temperature, and water was added to give a white precipitate. This was filtered to give 9.5 g of the title compound: MS m/z 311 (M++1), 310 (M+); 300-MHz ¹H NMR (DMSO-d₆) δ0.03 (s, 6 H), 0.85 (S, 9 H), 1.70–1.88 (m, 2 H), 2.27–2.38 (m, 1 H), 2.78–2.88 (m, 1 H), 3.16–3.27 (m, 1 H), 3.37–3.45 (m, 1 H), 3.49–3.58 (m, 1 H), 5.92 (b s, 2 H), 6.21 (b s, 1 H), 9.67 (b s, 1 H).

EXAMPLE 10

2-t-Butylcarbonylamino-4-hydroxy-6-[t-butyl(dimethyl)silyloxymethyl]-5,6,7,8-tetrahydropyrido[2,3-d]pyrimidine To a solution of 0.12 g 4-dimethylaminopyridine in 30 ml pivalic anhydride were added 3.0 g of 2-amino-4-hydroxy-6-[t-butyl(dimethyl)silyloxymethyl]-5,6,7,8-tetrahydropyrido[2,3-d]pyrimidine. The mixture was stirred for 6 hours at 90° C. and then for 8 hours at 22° C. The resulting solution was triturated with 30 ml ether to give a white precipitate. This was filtered to give 2.8 g of the title compound: MS m/z 395 (M++1), 394 (M+); 300-MHz ¹H NMR (CDCl₃) δ0.05 (s, 6 H), 0.90 (s, 9 H), 1.31 (s, 9 H), 2.02–2.12 (m, 1 H), 2.14–2.22 (m, 1 H), 2.64 (d of d, J=14, 4 Hz, 1 H), 3.16 (t, J=8 Hz, 1 H), 3.43–3.50 (m, 2 H), 3.70 (d of d, J=10, 4 Hz, 1 H), 4.65 (b s, 1 H), 7.83 (b s, 1 H).

EXAMPLE 11

2-t-Butylcarbonylamino-4-hydroxy-6-hydroxymethyl-5,6,7,8-tetrahydropyrido[2,3-d]pyrimidine To a mixture of 5.0 g of 2-t-butylcarbonylamino-4-hydroxy-6-[t-butyl(dimethyl)silyloxymethyl]-5,6,7,8-tetrahydropyrido[2,3-d]pyrimidine in 50 ml of THF and 50 ml of water were added 150 ml of glacial acetic acid. The mixture was stirred 18 hours at 22° C. and then evaporated to a viscous oil. Water was added and the resulting white precipitate collected by filtration to give 3.1 g of the title compound: mp 236°–238° C.; Anal. Calcd for C₁₉H₃₄N₄O₃Si: C, 55.70; H, 7.19; N, 19.99. Found: C, 55.96; H, 7.25; N, 19.69.

EXAMPLE 12

Methyl 4-benzyloxybenzoate

To a solution of 75 g of methyl 4-hydroxybenzoate in 700 ml THF at 22° C. were added 19.7 g of a 60% dispersion of sodium hydride in mineral oil. After the mixture was stirred for 90 minutes, 84.3 g of benzyl bromide was added dropwise. The reaction was heated at reflux for 18 hours, cooled to room temperature and 50 ml methanol was added. The mixture was evaporated and the resulting residue extracted with three portions of ethyl acetate. The combined organic extracts were washed with water and brine, dried over magnesium sulfate and evaporated to a solid. Recrystallization from cold methanol gave 28.7 g of the title compound: 300 MHz ¹H NMR (CDCl₃) δ3.96 (s, 3 H), 5.19 (s, 2 H), 7.05 (d, J=9 Hz, 2 H), 7.42 (s, 5 H), 8.05 (d, J=9 Hz, 2 H).

EXAMPLE 13

4-Benzyloxybenzoic acid

To a suspension of 15.0 g of methyl 4-benzyloxybenzoate in 225 ml of methanol were added 18.6 ml of a 5N solution of sodium hydroxide. The mixture was heated at reflux for 18 hours. The solution was cooled to room temperature and acidified to pH 3 by addition of 6N hydrochloric acid. The resulting white precipitate was filtered to give 13.6 g of the title compound: 300-MHz $^1$H NMR (DMSO-$d_6$) $\delta$5.18 (s, 2 H), 7.04 (d, J=9 Hz, 2 H), 7.26-7.49 (m, 5 H), 7.86 (d, J=9 Hz, 2 H), 12.3 (b s, 1 H).

EXAMPLE 14

N-(4-Benzyloxybenzoyl)-L-glutamic acid dimethyl ester

To a suspension of 10.0 g of 4-benzyloxybenzoic acid in 400 ml dichloroethane were added 10.5 g of thionyl chloride and 1 drop DMF. The mixture was heated at reflux for 2.5 hours under nitrogen. After cooling to room temperature, the solution was evaporated to a white solid. The resulting acid chloride was dissolved in 350 ml anhydrous dichloromethane and 8.5 g of L-glutamic acid dimethyl ester hydrochloride was added, followed immediately by dropwise addition of 8.9 g of triethylamine. The mixture was stirred for 18 hours at 22° C. and then washed with three portions of 1N hydrochloric acid, water and brine, dried over magnesium sulfate and evaporated to a white solid. Recrystallization from ethyl acetate triturated with cyclohexane gave 13.7 g of the title compound: mp 108°-109° C.; Anal. Calcd for $C_{21}H_{23}NO_6$: C, 65.44; H, 6.02; N, 3.63. Found: C, 65.28; H, 5.83; N, 3.53.

EXAMPLE 15

N-(4-Hydroxybenzoyl)-L-glutamic acid dimethyl ester

To a solution of 5.0 g of N-(4-benzyloxybenzoyl)-L-glutamic acid dimethyl ester in 175 ml ethanol and 25 ml ethyl acetate were added 0.6 g of 5% Pd/C. The mixture was shaken under a hydrogen atmosphere (3 atm) at 22° C. for 3 hours. The reaction mixture was then filtered through Celite and evaporated to an oil which was dissolved in ethyl acetate and, again, filtered through Celite. The filtrate was evaporated to give 3.8 g of the title compound as an oil: 300-MHz $^1$H NMR (CDCl$_3$) $\delta$2.10-2.21 (m, 1 H), 2.24-2.38 (m, 1 H), 2.41-2.58 (m, 2 H), 3.65 (s, 3 H), 3.79 (s, 3 H), 4.76-4.85 (m, 1 H), 6.86 (d, J=9 Hz, 2 H), 7.11 (d, J=10 Hz, 1 H), 7.67 (d, J=9 Hz, 2 H), 7.78 (b s, 1 H).

EXAMPLE 16

Dimethyl 2-pivaloyl-5-deaza-10-oxo-5,6,7,8-tetrahydrofolate

To a solution of 3.3 g of N-(4-hydroxybenzoyl)-L-glutamic acid dimethyl ester and 2.7 g of triphenylphosphine in 250 ml of anhydrous THF were added 2.4 g of 2-t-butylcarbonylamino-4-hydroxy-6-hydroxymethyl-5,6,7,8-tetrahydropyrido[2,3-d]pyrimidine. Diethyl azodicarboxylate (1.8 g) was added and the mixture was stirred for 2.5 hours at 22° C. A saturated solution of sodium bicarbonate (25 ml) was added and the reaction was evaporated to remove most of the THF. The residue was extracted with three portions of chloroform and the combined extracts were washed with water and brine, dried over magnesium sulfate and evaporated. The resulting oily residue was chromatographed over silica gel eluting with methanol in chloroform to give 1.6 g of the title compound: MS m/z 558 (M$^+$+1), 557 (M$^+$); 300-MHz $^1$H NMR (CDCl$_3$) $\delta$1.28 (s, 9 H), 2.09-2.21 (m, 1 H), 2.27-2.60 (m, 5 H), 2.72-2.81 (m, 1 H), 3.22-3.31 (m, 1 H), 3.45-3.56 (m, 1 H), 3.65 (s, 3 H), 3.79 (s, 3 H), 3.82-3.90 (m, 1 H), 3.98-4.05 (m, 1 H), 4.78-4.85 (m, 1 H), 5.06 (b s, 1 H), 6.90 (d, J=9 Hz, 2 H), 7.03 (d, J=10 Hz, 1 H), 7.79 (d, J=9 Hz, 2 H), 8.32 (b s, 1 H).

EXAMPLE 17

5-Deaza-10-oxo-5,6,7,8-tetrahydrofolic acid

A suspension of 2.0 g of dimethyl 2-pivaloyl-5-deaza-10-oxo-5,6,7,8-tetrahydrofolate in 30 ml of a 1N solution of sodium hydroxide was stirred for 36 hours at 22° C. The solution was acidified to pH 3.5 with 5N hydrochloric acid. The resulting precipitate was filtered to give 1.3 g of the title compound: MS m/z 447 (M$^+$+1), 446 (M$^+$); 300-MHz $^1$H NMR (DMSO-$d_6$) $\delta$1.86-2.22 (m, 4 H), 2.24-2.40 (m, 2 H), 2.42-2.54 (m, 1 H), 2.95-3.05 (m, 1 H), 3.24-3.36 (m, 1 H), 3.82-4.01 (m, 2 H), 4.28-4.40 (m, 1 H), 5.92 (b s, 2 H), 6.30 (b s, 1 H), 7.01 (d, J=9 Hz, 2 H), 7.83 (d, J=9 Hz, 2 H), 8.42 (d, J=10 Hz, 1 H), 9.75 (b s, 1 H).

EXAMPLE 18

Bis-[4-(N-L-glutamic acid dimethyl ester)carboxyphenyl]disulfide

To a suspension of 6.0 g of bis-(4-carboxyphenyl)disulfide in 100 ml dichloroethane were added 9.3 g of thionyl chloride. The mixture was heated at reflux for 2 hours under nitrogen. After cooling to room temperature, the solution was evaporated to a dark oil. The resulting acid chloride was dissolved in 125 ml anhydrous dichloromethane and 8.3 g of L-glutamic acid dimethyl ester hydrochloride was added, followed immediately by dropwise addition of 8.3 g of triethylamine. The mixture was stirred for 18 hours at 22° C. and then washed with three portions of 1N hydrochloric acid, water and brine, dried over magnesium sulfate and evaporated. The resulting oil was chromatographed over silica gel eluting with ethyl acetate in toluene to give 3.8 g of the title compound: MS m/z 621 (M$^+$+1), 620 (M$^+$), 619 (M$^+$-1); 300-MHz $^1$H NMR (CDCl$_3$) $\delta$2.07-2.20 (m, 2 H), 2.23-2.37 (m, 2 H), 2.42-2.55 (m, 4 H), 3.65 (s, 6 H), 3.79 (s, 6 H), 4.74-4.85 (m, 2 H), 7.17 (d, J=9 Hz, 2 H), 7.51 (d, J=9 Hz, 4 H), 7.78 (d, J=9 Hz, 4 H).

EXAMPLE 19

Dimethyl 2-pivaloyl-5-deaza-10-thio-5,6,7,8-tetrahydrofolate

To a solution of 0.20 g of 2-t-butylcarbonylamino-4-hydroxy-6-hydroxymethyl-5,6,7,8-tetrahydropyrido[2,3-d]pyrimidine and 0.43 g of tri-n-butylphosphine in 15 ml of DMF were added 1.3 g of bis-[4-(N-L-glutamic acid dimethyl ester)-carboxyphenyl]disulfide. The reaction was stirred for 36 hours at 22° C. and then evaporated. The residue was chromatographed over silica gel eluting with methanol in chloroform to give 0.09 g of the title compound: MS m/z 573 (M$^+$), 572 (M$^+$-1); Anal. Calc'd for $C_{27}H_{35}N_5O_7S$: C, 56.53; H, 6.15; N, 12.21; S, 5.59. Found: C, 56.95; H, 6.37; N, 11.81; S, 4.99.

EXAMPLE 20

5-Deaza-10-thio-5,6,7,8-tetrahydrofolic acid

A suspension of 0.08 g of dimethyl 2-pivaloyl-5-deaza-10-thio-5,6,7,8-tetrahydrofolate in 4 ml of a 1N solution of sodium hydroxide was stirred for 36 hours at 22° C. The solution was acidified to pH 3.5 with 5N hydrochloric acid. The resulting precipitate was filtered to give 0.04 g of the title compound: MS m/z 462 (M+), 309, 219, 155; 300-MHz $^1$H NMR (DMSO-d$_6$) δ1.81–2.15 (m, 4 H), 2.26–2.39 (t, J=6 Hz, 2 H), 2.50–2.59 (m, 1 H), 2.85–3.10 (m, 3 H), 3.21–3.30 (m, 1 H), 4.28–4.40 (m, 1 H), 5.94 (s, 2 H), 6.28 (s, 1 H), 7.39 (d, J=9 Hz, 2 H), 7.80 (d, J=9 Hz, 2 H), 8.52 (d, J=10 Hz, 1 H), 9.70 (b s, 1 H).

We claim:

1. A compound of the formula

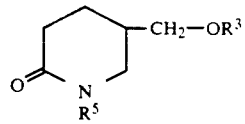

wherein
 $R^3$ is H or a hydroxyl protecting group; and
 $R^5$ is H or an amino protecting group.

2. A compound according to claim 1, wherein $R^3$ is a tri-lower alkylsilyl.

3. A compound according to claim 2, wherein $R^3$ is t-butyldimethylsilyl.

4. A compound according to claim 1, wherein $R^3$ is H.

5. A compound according to claim 1, wherein $R^5$ is an amino protecting group.

6. A compound according to claim 5, wherein $R^5$ is N-alkoxycarbonyl.

7. A compound according to claim 6, wherein $R^5$ is N-(t-butyloxycarbonyl).

8. A compound according to claim 1, wherein $R^5$ is H.

9. A compound according to claim 7, wherein $R^3$ is t-butyldimethylsilyl.

10. A compound according to claim 8, wherein $R^3$ is t-butyldimethylsilyl.

11. A compound according to claim 8, wherein $R^3$ is H.

* * * * *